United States Patent
Dragotta

(10) Patent No.: US 6,765,675 B2
(45) Date of Patent: Jul. 20, 2004

(54) FLUID INSPECTION APPARATUS WITH VIBRATOR

(75) Inventor: Peter J. Dragotta, Wayne, NJ (US)

(73) Assignee: M. W. Technologies, Inc., Elmwood Park, NJ (US)

( * ) Notice: Subject to any disclaimer, the term of this patent is extended or adjusted under 35 U.S.C. 154(b) by 452 days.

(21) Appl. No.: 09/766,908

(22) Filed: Jan. 22, 2001

(65) Prior Publication Data

US 2001/0033372 A1 Oct. 25, 2001

Related U.S. Application Data

(60) Provisional application No. 60/182,174, filed on Feb. 14, 2000.

(51) Int. Cl.⁷ .............................................. G01N 21/88
(52) U.S. Cl. ................................... 356/427; 356/239.6
(58) Field of Search ........................ 356/427, 239.6; 250/223 B; 209/524, 526

(56) References Cited

U.S. PATENT DOCUMENTS

| | | | |
|---|---|---|---|
| 3,777,169 A | * 12/1973 | Walter et al. | ............... 250/565 |
| 3,858,851 A | * 1/1975 | Ogle | ........................ 356/336 |
| 4,158,625 A | * 6/1979 | Takahashi et al. | .......... 356/427 |
| 4,258,625 A | * 3/1981 | Black | ........................ 102/503 |
| 4,902,137 A | * 2/1990 | Krieg et al. | ................ 356/427 |
| 5,523,560 A | * 6/1996 | Manique et al. | ........ 250/223 B |

* cited by examiner

Primary Examiner—Richard A. Rosenberger
(74) Attorney, Agent, or Firm—Anthony J. Casella; Gerald E. Hespos

(57) ABSTRACT

An apparatus is provided for optically inspecting containers of liquid solutions. The apparatus includes a fixture for gripping the container and a conveyor or indexable table for moving the fixtured container into alignment with a camera or other optical inspection device. The apparatus further includes a vibrator at the inspection station. The vibrator causes the container of the liquid solution to vibrate sufficiently for extraneous material in the solution to move into a position that permits accurate visual inspection.

6 Claims, 2 Drawing Sheets

FLUID INSPECTION APPARATUS WITH VIBRATOR

This application claims priority on U.S. Provisional Patent Application No. 60/182,174, filed Feb. 14, 2000.

BACKGROUND OF THE INVENTION

1. Field of the Invention

The subject invention relates to an apparatus and method for high speed optical inspection of fluids, such as liquid pharmaceutical products that may be stored in syringes, vials or other such containers.

2. Description of the Related Art

Liquid pharmaceutical products must be manufactured and packaged under carefully controlled conditions to prevent extraneous material from being incorporated into the finished product. Despite these careful manufacturing and packaging controls, most pharmaceutical companies perform a final optical inspection in an effort to identify any extraneous material that might have been incorporated inadvertently into the sealed container of the liquid pharmaceutical product. Such optical inspections are intended to identify any undissolved granular material, fibers or the like.

A typical prior art optical inspection apparatus for these purposes includes a small video camera directed at the container of liquid pharmaceutical. The camera is connected to a video monitor which displays a magnified and illuminated image of the liquid pharmaceutical in the container. The image displayed on the monitor enables an inspector to identify containers of the liquid pharmaceutical products with extraneous materials. These packages then can be rejected and discarded. Additionally, the inspection apparatus may be used to identify sources of contamination. Corrective measures then may be incorporated into the manufacturing and packaging process.

The optical inspection of liquid pharmaceutical products typically is carried out for each packaged product, and not merely for a representative sample. Accordingly, the inspection must be carried out very quickly. A typical optical inspection is performed with an apparatus that rapidly advances a container into the viewing field of the camera, temporarily interrupts the movement of the apparatus to enable an optical inspection and then quickly moves the container to a location for further packaging or to a location for discard.

Extraneous material in a liquid pharmaceutical product will tend to settle at the bottom of the container, and there is a substantial risk that the inspection method will not detect a small extraneous particle that has settled to the base of the container. Prior art optical inspection devices have recognized the problems associated with the settling of extraneous matter in liquid pharmaceuticals. Thus, prior art devices have included mechanisms to move any extraneous matter from the bottom of the container into a more central position in the container where optical inspection is more accurate and reliable. For example, one prior art apparatus is operative for quickly inverting the container immediately prior to the optical inspection. This inversion is intended to cause any extraneous material to move gravitationally within the liquid from a location spaced from the location that had originally defined the gravitational bottom of the container. The extraneous material can be observed due to its movement and to its location in a more central position in the container.

Other prior art inspection devices spin the container of the liquid pharmaceutical product about a vertical axis. The spinning of the container causes extraneous material in the liquid pharmaceutical product to move from its settled location adjacent the bottom of the container to a location spaced from the bottom of the container. This movement of the extraneous material and the more central location of the extraneous material facilitates the optical inspection process and improves accuracy of inspections.

Both of the prior art devices for generating movement of extraneous material in liquid pharmaceuticals perform their intended function well, but have certain drawbacks. In particular, the prior art apparatus for inverting the container or for spinning the container is fairly complex and requires a substantial amount of space on the inspection apparatus. Thus, machines to perform these optical inspections are undesirably large and take up valuable space in the manufacturing or packaging facility. Additionally, the potential exists for damaging portions of the container during the inversion or spinning. In this regard, some such containers are small flexible plastic containers that have a small needle cannula pre-mounted thereon. The container may be formed from a flexible material that permits injection by squeezing opposite walls of the container. These small flexible containers with small needle cannulas can be damaged by the rapid inversion or spinning. Furthermore, inversion and spinning both take time, thereby slowing the inspection process.

In view of the above, it is an object of the subject invention to provide an inspection apparatus that enables accurate optical inspections that are capable of detecting extraneous materials in liquid solutions.

It is another object of the subject invention to provide an inspection apparatus that enables extraneous materials in liquid solutions to move without spinning or inverting the containers of these solutions.

SUMMARY OF THE INVENTION

The subject invention is directed to an inspection apparatus for optically inspecting liquid solutions. The apparatus may include an indexable fixture for receiving containers of a liquid solution to be inspected and for sequentially indexing the containers into a location for inspection. The apparatus may further include loading means for selectively loading the containers into the indexable fixture. The loading means may be automated and high speed and may be constructed to ensure accurate positioning of the containers in the fixture. The apparatus may further include at least one optical inspection station at one or more locations in proximity to the indexable fixture. The optical inspection station may include at least one light source and at least one video camera. The video camera may be connected electronically to a video monitor that provides a video display of a container that is indexed into the inspection station.

The apparatus of the subject invention further includes at least one vibrator in proximity to the indexable fixture. The vibrator is operative to generate vibrations that are sufficient to agitate the liquid solution in the container and to generate movement of any extraneous material in the liquid solution. The amplitude and frequency of vibration may be selected in accordance with characteristics, such as viscosity of the liquid solution being inspected. In some embodiments, the vibrator may be variable so that the frequency and amplitude can be adjusted. Additionally, the vibrator may be intermittently operative. In particular the vibrator may be terminated after a selected time based on the indexing of the fixture, or the vibrator may be terminated in response to a signal from a technician using the apparatus. The termination of the vibration will permit the technician to observe a stationary container. However, any extraneous material in the liquid solution will remain in motion despite the termination of the vibration, and hence will be readily observable.

The apparatus may include means for identifying unacceptable containers for discard. The apparatus may further include means for ejecting containers that have been identified as unacceptable. Finally, the apparatus may include means for advancing acceptable containers from the indexable fixture to a location for further packaging or use.

The apparatus of the subject invention provides several significant advantages over the prior art. In particular, the vibrator can be small and can be spaced at least a small distance from the container to be inspected. Thus, the entire apparatus can be more compact than an apparatus that relies upon inversion or spinning of the container, or other such prior art apparatus that requires complex mechanisms to be incorporated into the fixture for generating such movement. Additionally, the minor vibration enabled by the subject apparatus is less likely to damage fragile containers or needle cannulas. Furthermore, the vibration does not add significantly to the inspection cycle time. Finally, vibration amplitude and frequency can be selected to generate movement of extraneous particles without generating bubbles or excessive turbulence that could give rise to false indications of extraneous materials. Bubbles or turbulence could be generated, however, by the prior art apparatus that rapidly inverts or spins the container.

DETAILED DESCRIPTION OF THE PREFERRED EMBODIMENT

Figure 1:
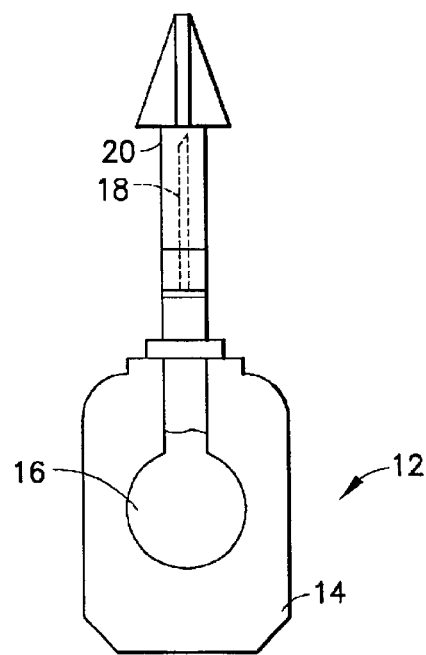
FIG. 1 is a front elevational view of a prior art container for a liquid pharmaceutical solution.
Figure 2:
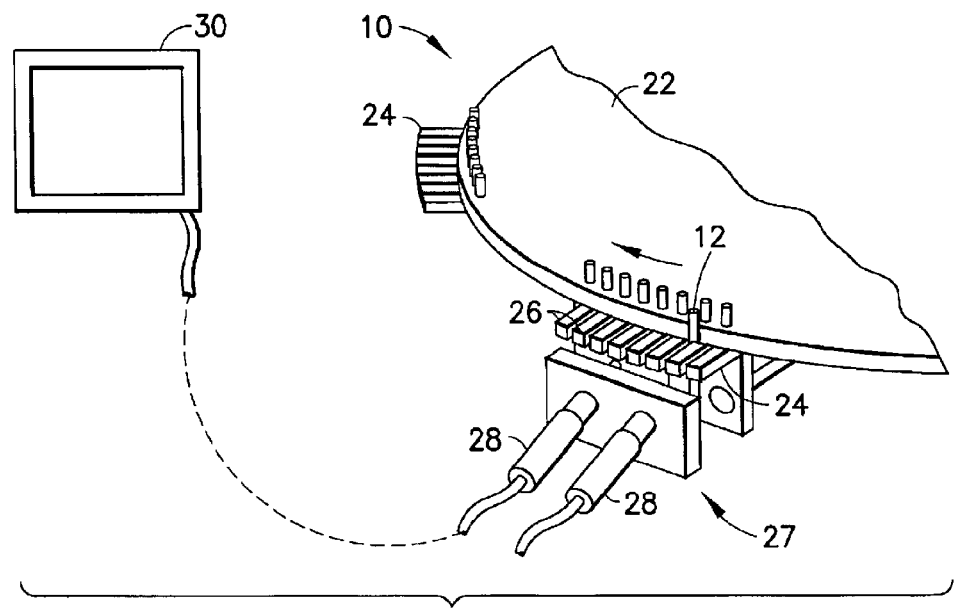
FIG. 2 is a perspective view of an indexable inspection apparatus in accordance with the subject invention.

An inspection apparatus in accordance with the subject invention is identified generally by the numeral 10 in FIG. 2. The inspection apparatus 10 is intended for optically inspecting small pre-filled hypodermic syringes, which are identified generally by the numeral 12 in FIG. 1. The syringe 12 is formed from two sheets of flexible plastic material 14 and 16 that are secured to one another about registered peripheral edges thereof. Central portions of the sheets of plastic material effectively define a bubble into which a selected dose of a liquid pharmaceutical product is preloaded. A needle cannula 18 is mounted to the container 12 and is covered by a safety cap 20. The syringe 12 can be used by removing the safety cap 20 and inserting the needle cannula 18 into a patient. Portions of the registered sheets of transparent plastic film 14 that define the bubble 16 may be squeezed to inject the pre-selected dosage of pharmaceutical material into the patient. The apparatus 10 is operative for optically inspecting a plurality of syringes 12 or other such containers to identify any extraneous material that may have inadvertently been loaded into the bubble 16. Thus, the apparatus 10 enables containers with extraneous material to be identified as unacceptable and then rejected.

As shown most clearly in FIG. 2, the apparatus 10 includes an indexable table 22 with a plurality of fixtures 24 each of which is configured to releasably retain a plurality of syringes 12 in specified and carefully controlled positions and orientations. In the embodiment shown herein, each fixture 22 is configured to receive four such syringes 12. However, more or fewer syringes 12 may be retained in such a fixture. Each fixture 24 includes pairs of gripping fingers 26. Each pair of gripping fingers 26 is operative for securely holding a syringe 12 in a selected position and orientation.

The apparatus 10 further includes an inspection station 27 with video cameras 28 aligned to optically inspect the respective syringes 12 and to generate an image of each inspected syringe 12 on at least one monitor 30. The inspection station 27 further includes at least one light source 29 disposed on a side of the respective syringes 12 opposite the video cameras 28. The light sources 29 function to illuminate the liquid solution in the syringes 12 sufficiently for effective viewing by the video camera 28. The light sources 29 may be provided with filters of a color selected in accordance with characteristics of the liquid solution in the syringes 12. The apparatus 10 is operative to selectively and sequentially index the fixtures 24 into the inspection station 27 for alignment with the respective cameras 28 to enable the cameras 28 to view the syringe 12 aligned therewith.

Figure 3:
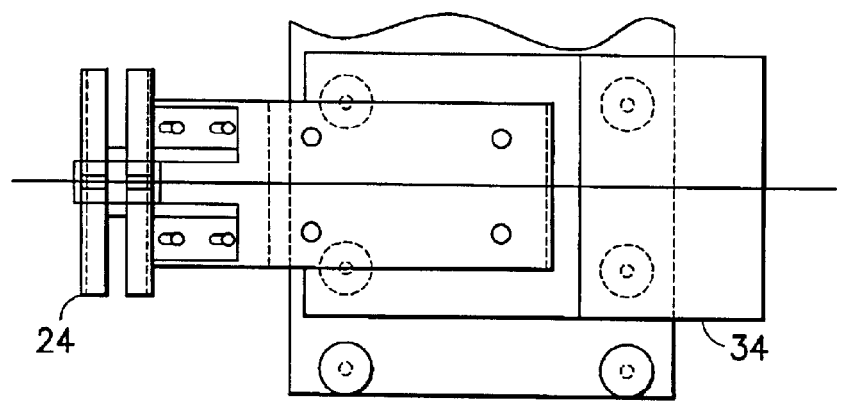
FIG. 3 is a top plan view of the fixturing apparatus shown in FIG. 2.
Figure 4:
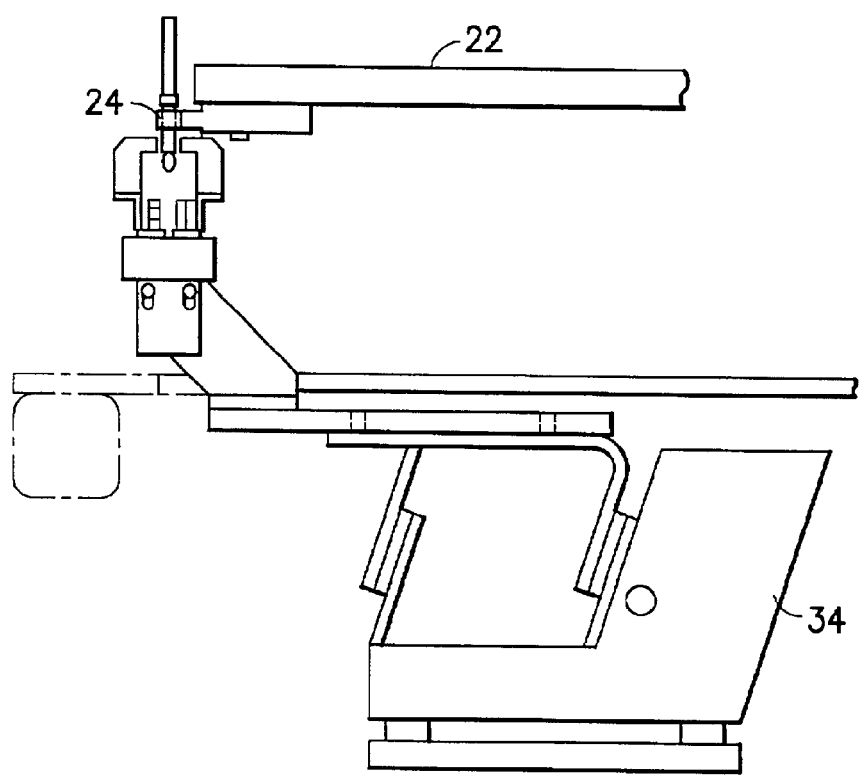
FIG. 4 is a side elevational view of the fixturing apparatus.

As shown most clearly in FIGS. 3 and 4, the apparatus 10 includes a vibrator 34. The vibrator 34 is operative to vibrate the fixture 24 as the fixture is indexed into the inspection station 27. The vibration is of sufficient amplitude, duration and frequency to cause minor agitation of the liquid pharmaceutical product in the syringe 12 that is sufficient to move any extraneous material therein into a more central position within the syringe 12. The vibrator 34 further is operative to stop vibrating as the fixture reaches the inspection station, or shortly after the fixture has reached the inspection station. The termination of the vibration will enable the inspection to be carried out on the stationary syringe 12. However, any extraneous material in the liquid solution may still be in motion due to the inertial effect of the previously applied forces of the vibrator 34. Thus, the moving extraneous material in the syringe 12 can be observed while the syringe 12 is stationary. Under these circumstances, any extraneous material is easily observable. The centrally disposed and/or moving extraneous material then can be visually detected on the monitor 30, and any syringe 12 with such extraneous material can be identified as unacceptable. Unacceptable syringes 12 may be discarded, and acceptable syringes 12 may be advanced for further packaging as the fixture 24 is indexed beyond the inspection station 27.

While the invention has been described with respect to a preferred embodiment, it is apparent that various changes can be made without departing from the scope of the invention as defined by the appended claims.

For example, the illustrated embodiment shows only one vibrator. However, a plurality of vibrators may be provided. The apparatus may include an upstream vibrator for imparting a vibration to the fixture before the fixture reaches the inspection station. The duration of vibration imparted by the upstream vibrator may be variable. The upstream vibrator may be particularly useful for liquid solution having a high viscosity and requiring greater amount of vibration to enable accurate observation of extraneous material in the solution. The provision of the upstream vibrator will enable sufficient vibration without unnecessarily adding to the dwell time at the inspection station.

What is claimed is:

1. An apparatus for optical inspection of liquid solutions and for identifying extraneous materials in such solutions, said apparatus comprising:

an inspection station having at least one light source;

an indexable fixture for securely gripping at least one container of the liquid solution at a location spaced from the inspection station;

a vibrator spaced from the inspection station for vibrating the fixture sufficiently to move extraneous material in the liquid solution in the container; and means for selectively moving the indexable fixture into the inspection station and into alignment with the light source and for terminating operation of the vibrator in the inspection station, thereby enabling visual inspections of a stationary container to identify the extraneous material moving in the liquid solution illuminated by the light source while maintaining a short dwell time in the inspection station.

2. The apparatus of claim 1, wherein the light source comprises a colored filter for enhancing visibility of extraneous matter in the solution.

3. The apparatus of claim 1, further comprising a video camera and a video monitor for generating an optical image of the containers of the liquid solution in the inspection station.

4. An inspection method comprising:

providing a plurality of substantially transparent containers, each said container having a liquid solution therein;

placing the containers in a selected orientation in a fixture;

vibrating the fixture sufficiently to cause any extraneous material in the liquid solution to move;

indexing the fixture to an inspection station while terminating the vibrating of the fixture;

illuminating the containers in the fixture;

identifying containers having extraneous material suspended in the liquid solution; and separating any of the containers that are identified to have the extraneous material therein.

5. The method of claim 4, further comprising providing a video camera at the inspection station and producing a viewable image of the respective containers passing into the inspection station.

6. The method of claim 4, wherein the step of vibrating the fixture is carried out to maintain the container in the selected orientation in the fixture.

* * * * *